United States Patent [19]

Lowrie et al.

[11] Patent Number: 4,645,858
[45] Date of Patent: * Feb. 24, 1987

[54] PENTANEDIOIC ACID DERIVATIVES

[75] Inventors: Harman S. Lowrie, Northbrook; John S. Baran, Winnetka, both of Ill.

[73] Assignee: G. D. Searle & Co., Skokie, Ill.

[*] Notice: The portion of the term of this patent subsequent to Nov. 19, 2002 has been disclaimed.

[21] Appl. No.: 786,027

[22] Filed: Oct. 10, 1985

Related U.S. Application Data

[63] Continuation of Ser. No. 577,411, Feb. 6, 1984, abandoned, which is a continuation-in-part of Ser. No. 360,543, Mar. 22, 1982, abandoned.

[51] Int. Cl.$^4$ .......................................... C07C 59/245
[52] U.S. Cl. ................................... 562/582; 562/470; 562/508; 562/509
[58] Field of Search ................ 562/470, 508, 509, 582

[56] References Cited

U.S. PATENT DOCUMENTS 3,818,080 6/1974 Baran et al. ..................... 562/470 X
4,554,359 11/1985 Lowrie et al. .................. 562/508 X Primary Examiner—Natalie Trousof
Assistant Examiner—Patricia M. Scott
Attorney, Agent, or Firm—John McDonnell; Steven Odre

[57] ABSTRACT

Compounds of formula I are described which are useful to inhibit the formation of serum cholesterol by virtue of their ability to inhibit β-hydroxy-β-methylglutaryl-CoA(HMG CoA), the rate-controlling substance in the synthesis of serum cholesterol.

4 Claims, No Drawings

PENTANEDIOIC ACID DERIVATIVES

This is a continuation of application Ser. No. 577,411 filed Feb. 6, 1984 which is a continuation in-part of Ser. No. 360,543, filed Mar. 22, 1982, now abandoned.

BACKGROUND OF THE INVENTION

The invention relates to novel pentanedioic acid derivatives. In particular, it relates to novel pentanedioic acid derivatives of formula I which are useful to inhibit the formation of serum cholesterol. The novel compounds exhibit this utility by virtue of their ability to inhibit the activity of $\beta$-hydroxy-$\beta$-methylglutaryl coenzyme A (HMG CoA) and thus inhibit the formation of serum cholesterol. HMG CoA is a substance which controls the rate at which cholesterol is synthesized in mammalian liver (one of the two principal in vivo sources of serum cholesterol). Thus the compounds of the instant invention are useful to inhibit sterol biosynthisis in individuals predisposed to familial type hypercholesterolemia. The significance of such compounds is widely recognized, e.g. Breslow et al. Biochim. Biophys. Acta, 398,10(1975); Betheridge et al., Brit. Med. J., 4,500 (1975); and Brown et al., J. Biol. Chem. 249, 7306(1974).

PRIOR ART

The use of agents which lower serum cholesterol are widely described in the art as described above. Pentanedioic acid derivatives are known in the art, for example, U.S. Pat. No. 3,818,080 which describes a wide variety of compounds useful for their antiulcerogenic activity. The compounds actually made are either toxic or relatively inactive when compared with the compounds of the invention in their ability to control serum cholesterol.

SUMMARY OF THE INVENTION

The present invention particularly provides compounds of formula I:

$$R_2-\underset{\underset{R_3}{|}}{\overset{\overset{R_1}{|}}{C}}-(CH_2)_n\overset{\overset{OH}{|}}{C}(CH_2CO_2H)_2$$

wherein $R_1$ is:
(a) hydrogen; or
(b) methyl;
wherein $R_2$ is:
(a) methyl;
(b) ethyl;
(c) hydrogen only when $R_3$ is phenyl; or
(d) combined with $R_3$ to form a cyclohexyl ring;
wherein $R_3$ is:
(a) methyl;
(b) ethyl;
(c) phenyl; or
(d) combined with $R_2$ to form a cyclohexyl ring;
wherein n is an integer from 8 to 13, inclusive;

The utility of the instant compounds and their inhibition of the formation of serum cholesterol can be demonstrated via the following standardized test procedures:

Male Charles River CD rates initially weighing 180–250 g apiece are randomized in groups of 6, housed in a reverse light cycle (12:12) room, and maintained therein on a standard rat diet plus water ad libitum.

To each animal in a group, after at least 3, but not more than 6 days, 5 mg/kg of 20,25-diazacholesterol dissolved in 0.2 ml of physiological saline containing 0.1 percent of polyoxyethylene sorbitan monooleate (Tween 80) is intragastrically administered on each of 7 consecutive days, during the last 4 of which the test compound is concurrently and identically administered at a pre-selected, daily dose (commonly 5 mg/kg intragastrically). Controls are provided by a second group of animals identically treated except that test compound is omitted. Within 2–4 hr after treatment is completed, and 5–7 hrs. into the dark cycle, the animals are anesthetized with diethyl ether and thereupon killed. Livers are quickly removed, washed with a chilled homogenization medium (preparable by dissolving 102.7 g of sucrose, 3.8 g of sodium edetate, and 0.8 g of dithiothreitol in water q.s. 1000 ml), blotted dry, weighed, and homogenized (using 2 ml of the aforesaid chilled medium for each g of liver). The homogenates are centrifuged at 4°±C. and 15,000×g for 15 min., whereupon the supernatants are separated and centrifuged at 4°± C. and 100,000×g for 60 min. The resultant supernatants are discarded and the residues suspended in half the volume of homogenization medium previously employed (i.e., 1 ml for each gram of residue). HMG CoA reductase activity is assayed substantially in accordance with procedures described by L. W. White et al. in Biochemistry, 9, 2713 (1970); P. A. Edwards et al. in Biochim. Biophys. Acta, 409, 39 (1975).

Protein is determined by the method of O. H. Lowry et al., J. Biol. Chem., 193, 265 (1951). The data obtained is converted to specific activity (mmol/20 min./mg protein) for each animal, from which group mean(s) and percent change, relative to controls, are calculated. A statistically significant response (P 0.05) is the criterion for HMG CoA reductase inhibition/stimulation. Compounds of the formula:

$$\underset{}{\bigcirc}-(CH_2)_{10}-\overset{\overset{OH}{|}}{C}(CH_2CO_2H)_2$$

are active with an IC$_{50}$ of 52 $\mu$M while a compound of the prior art of the formula:

$$\underset{}{\bigcirc}-CH_2-\underset{\underset{CH_2COOH}{|}}{\overset{\overset{OH}{|}}{C}}-CH_2COOH$$

is inactive at concentrations at least up to 1000 $\mu$m.

In vivo activity is tested as follows:

Initial serum total cholesterol, triglycerides, and lipoprotein cholesterol values are determined 3 times for each male Rhesus monkey used before treatment with a test compound begins. The test compound is administered in an initial dose of 60 mg/kg for 2 weeks and blood samples are taken to determine if rebound occurs. A dose is rated active if the 14-day mean values are significantly reduced from the pretreatment values (p 0.05). Statistical comparisons are made using the two tailed student's test.

A compound of the formula:

$$CH_3-\underset{\underset{CH_3}{|}}{\overset{\overset{CH_3}{|}}{C}}-(CH_2)_{11}-\overset{\overset{OH}{|}}{C}(CH_2CO_2H)_2$$

at 60 mg/kg/day reduced serum cholesterol 30% after 14 days of treatment while compounds of the prior art of the formula:

$$CH_3(CH_2)_{14}-\overset{\overset{OH}{|}}{C}(CH_2CO_2H)_2$$

at 60 mg/kg/day resulted in acute toxicity in 2 of 4 monkeys.

By virtue of this activity the compounds of formula I are useful in treating type 2 hypercholesterolemia (TTH-2) in humans and animals. A physician or veterinarian of ordinary skill could readily determine a subject who has TTH-2 symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally, vaginally in such forms as suppositories, interparenterally, subcutaneously, or intramuscularly, using forms known to the pharmaceutical art. In general, the preferred form of administration is orally.

An effective but non-toxic quantity of the compound is employed in treatment. The dosage regimen for preventing or treating TTH-2 by the compounds of this invention is selected in accordance with a variety of factors including the type, age, weight, sex, and medical condition of the mammal, the severity of the TTH-2, the route of administration and the particular compound employed. An ordinarily skilled physician or veterinarian will readily determine and prescribe the effective amount of the Anti-TTH-2 agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 10 mg/kg up to 200 mg/kg orally. When other forms of administration are employed equivalent doses are administered.

The general procedure for producing the compounds of the instant invention is outlined on Chart A. It is similar to the general procedure used to produced the compounds of U.S. Pat. No. 3,818,080 herein incorporated by reference. The carboxylic esters used as starting materials, which are not readily available from commercial sources or by esterification of available acids, can be prepared by for example the routes outlined on Chart B. One skilled in the art could readily substitute appropriately for the R groups and complete the reaction based on the chart or deduced without undue experimentation after viewing the following representative examples. Temperature is in degrees Celcius unless otherwise stated.

DESCRIPTION OF THE PREFERRED EMBODIMENTS

The operation of this invention is further elaborated by the representative examples below:

EXAMPLE 1

11-(Triphenylphosphonium)undecanoic acid bromide $(C_6H_5)_3P^{\oplus}(CH_2)_nCO_2H \; Br^{\ominus}$ A mixture of 137 g of 11-bromoundecanoic acid and 137 g of triphenylphosphine is stirred for two days under nitrogen in 2 l of dry refluxing toluene. Overnight cooling, ca 0°, gives oily crystals from which toluene is removed by decanting. Washing with ether gives ca. 275 g of crude product. Recrystallization by precipitation from dichloromethane using diethyl ether produces a white powder, m.p. 86°–90°. Structure assignment of the product compound is supported by elemental analysis and by infrared and nmr spectroscopy.

In like manner homologous ω-bromoalkanoic acids as 6-bromohexanoic acid, 9-bromononanoic acid, 10-bromodecanoic acid, or 12-bromododecanoic acid may be reacted with triphenylphosphine to yield the corresponding phosphonium bromides. Structure assignments are supported by elemental analysis and by infrared and nmr spectroscopy.

n=10 Chart B. tlc (95:5 by volume of chloroform/methanol) using Merck silica gel): $R_f$ ca. 0.1–0.2.
Infrared ($CHCl_3$): ca. 1710 cm$^{-1}$ (carbonyl), ca. 2860, 2900 cm$^{-1}$ (alkane).
nmr [$(CD_3)_2SO$] (δ, ppm): 1.25 (s, methylene), 1.0–1.9 (m, methylene,) 2.20 (t, —$CH_2CO$—), 7.9 (d, $C_6H_5$—).
Elemental: Calcd. for $C_{29}H_{36}BrO_2P$: C,66.03; H, 6.88; P, 5.87. Found: C, 66.36; H, 6.95; P, 5.66.
m.p.: 87°–93° n=11 Chart B. tlc (95:5 by volume of chloroform/methanol) using Merck silica gel): $R_f$ ca. 0.1–0.2.
Infrared ($CHCl_3$): ca. 1710 cm$^{-1}$ (carbonyl), ca. 2860, 2900 cm$^{-1}$ (alkane).
nmr [$(CD_3)_2SO$] (δ, ppm): 1.25 (s, methylene) 1.0–1.9 (m, methylene) 2.20 (t, —$CH_2CO$—), 7.9 (d, $C_6H_5$—).

n=9 Chart B. tlc (95:5 by volume of chloroform/methanol) using Merck silica gel): $R_f$ ca. 0.1–0.2
Infrared ($CHCl_3$): ca. 1710 cm$^{-1}$ (carbonyl), ca. 2860, 2900 cm$^{-1}$ (alkane).
nmr [$(CD_3)_2SO$] (δ, ppm): 1.25 (s, methylene), 1.0–1.9 (m, methylene) 2.20 (t, —$CH_2CO$—): 7.9 (d, $C_6H_5$—).

n=8 Chart B. tlc (95:5 by volume of chloroform/methanol) using Merck silica gel): $R_f$ ca. 0.1–0.2.
Infrared ($CHCl_3$): ca. 1710 cm$^{-1}$ (carbonyl), ca. 2860, 2900 cm$^{-1}$ (alkane).
nmr [$(CD_3)_2SO$] (δ, ppm): 1.25 (s, methylene), 1.0–1.9 (m, methylene), 2.20 (t, —$CH_2CO$—), 7.9 (d, $C_6H_5$—).

n=5 Chart B. tlc (95:5 by volume of chloroform/methanol) using Merck silica gel): $R_f$ ca. 0.1–0.2.

Infrared (CHCl₃): ca. 1710 cm⁻¹ (carbonyl), ca. 2860, 2900 cm⁻¹ (alkane).

nmr [(CD₃)₂SO] (δ, ppm): 1.25 (s, methylene), 1.0–1.9 (m, methylene), 2.20 (t, —CH₂CO—), 7.9 (d, C₆H₅—).

EXAMPLE 2

11-(Cyclohexylidene)undecanoic acid

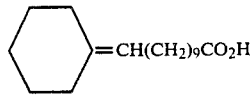

To 28.8 g (0.60 mole) of 50 percent sodium hydride in mineral oil is added, under a nitrogen atmosphere, 400 ml of dry dimethylsulfoxide, and the mixture is heated at 65° C. until gas evolution ceases within ca. ½ hour. The mixture is cooled to 25° to 30° and a solution of 158.2 g (0.30 mole) of 11-(triphenylphosphonium)undecanoic acid bromide in 500 ml of dimethylsulfoxide is added dropwise at less than 30°. After addition is completed, the mixture is diluted with 900 ml of dry tetrahydrofuran and cooled to 0° to 5° and a solution of 41.2 g (0.42 mole) of cyclohexanone in 300 ml of tetrahydrofuran is added dropwise with stirring to the above mixture, the temperature being kept at less than 5°. After addition is completed, the stirred reaction mixture is allowed to warm to room temperature for 18 to 24 hours. The mixture is then diluted with water and acidified with dilute sulfuric acid, and the product is extracted using two portions of Skellysolve B. When the organic layer is washed thoroughly with four portions of dilute sulfuric acid, an oily material containing triphenylphosphine oxide separates and is discarded. The remaining organic layer is dried with anhydrous sodium sulfate, concentrated to an oil dissolved in 50 ml of warm Skellysolve A. The white crystalline (10-carboxydecyl)diphenylphosphine oxide which precipitates upon cooling to 0° is collected and discarded. The solution in Skellysolve A is diluted to one 1 with additional Skellysolve A, decolorized with charcoal and filtered. The solvent is evaporated and the residue dried in vacuo to give 66.5 g of product as homogeneous, oily white plates. The compound is used for subsequent reactions without further purification, but could be recrystallized from Skellysolve A to yield large, shiny plates, mp. 42°–47°.

tlc (50:48:2 by vol. of toluene/ethyl acetate/acetic acid using Merck silica gel): R_f ca. 0.8

Infrared (CHCl₃): ca. 1720 cm⁻¹ (carbonyl), ca. 2860, 3000 cm¹ (alkane).

nmr (CDCl₃ (δ, ppm): 1.25 (s, methylene) over 0.9–1.9 (m, cyclohexyl), 2.70 (s, —CH₂CO₂—).

Elemental: Calcd. for C₁₇H₃₀O₂: C, 76.63; H, 11.35. Found: C, 76.46; H, 11.30.

m.p. 42°–47°.

EXAMPLE 3

Methyl 11-(cyclohexylidene)undecanoate

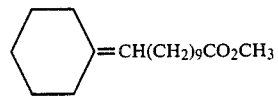

The methyl ester of 11-(cyclohexylidene)undecanoic acid is prepared by dissolving 66.5 g of the carboxylic acid in 300 ml of methanol to which is then added 1 ml of thionyl chloride. After three hours at room temperature, the solution is concentrated in vacuo, dissolved in Skellysolve A, and washed with dilute sodium bicarbonate. After residual solids are removed by filtration, the solution is washed with water, dried, decolorized with charcoal and filtered, and concentrated by evaporation of solvent. The oily residue is distilled at reduced pressure. Fractions with a boiling range of 134° to 137° at 0.07 mm Hg afford 48.4 g of product as a colorless oil. Structure assignment is supported by elemental analysis and by infrared and nmr spectroscopy.

tlc (90:10 by volume of Skellysolve B/ethyl acetate) using Merck silica gel): R_f ca. 0.6.

Infrared (CHCl₃): ca. 1760 cm⁻¹ (carbonyl), ca. 2860, 2940 cm⁻¹ (alkane).

nmr (CDCl₃) (δ, ppm): 1.28 (s, methylene), 1.3–1.8 (m, cyclohexyl) 2.15 (t, —CH₂CO—), 3.65 (s, CH₃O—), 4.8–5.25 (m, C=CH—).

Elemental: Calcd. for C₁₈H₃₂O₂: C, 77.09; H, 11.50. Found: C, 76.50, H, 11.43.

EXAMPLE 4

Methyl 11-(cyclohexyl)undecanoate

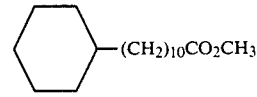

Hydrogenation of methyl 11-(cyclohexylidene)undecanoate (39.4 g) is effected in tetrahydrofuran at room temperature under 2 p.s.i. hydrogen using 5 percent palladium on charcoal as catalyst. Upon removal of insolubles by filtration, the mixture is concentrated in vacuo. The residue is dissolved in Skellysolve A, decolorized over charcoal and filtered. The solvent is evaporated and the residue is distilled at reduced pressure. Those fractions having a boiling range of 142° to 144° at 0.4 mm Hg pressure afford 36.6 g of product as a colorless oil. Structure assignment is supported by elemental analysis and by infrared and nmr spectroscopy.

tlc (90:10 by volume of Skellysolve B/ethyl acetate using Merck silica gel): R_f ca. 0.5.

Infrared (CHCl₃): ca. 1760 cm⁻¹ (carbonyl), 1850, 1930 cm⁻¹ (alkane).

nmr (CDCl₃) (δ, ppm): 1.25 (s, methylene), 1.4–2.2 (m, cyclohexyl), 2.3 (t, CH₂CO—), 3.63 (s, CH₃O—).

Elemental: Calcd. for C₁₈H₃₄O₂; C, 76.54; H, 12.13 Found: C, 76.92; H, 12.11.

EXAMPLE 5

1,1-Bis(allyl)-11-cyclohexylundecanol

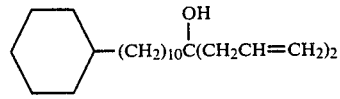

To an excess of magnesium metal (2.8 g) stirred in 250 ml of dry tetrahydrofuran under a nitrogen atmosphere is added 2 ml each of allyl bromide and allyl magnesium bromide (1M in diethyl ether) and a catalytic amount of iodine. After the reaction begins, a solution of 14.1 g of methyl 11-cyclohexylundecanoate and 13.9 g of allyl bromide in 50 ml of dry tetrahydrofuran is added dropwise to the reaction vessel. The reaction mixture is heated at reflux for ca. 1 hour, after which the reaction is quenched with methanol. The mixture is diluted with diethyl ether and washed with saturated aqueous ammonium chloride. The solution is dried, filtered, and concentrated in vacuo to an oil. Drying the oil at reduced pressure (2 mm Hg, 40°) gives 16.8 g of the carbinol product. Structure assignment is supported by infrared and nmr spectroscopy.

tlc (90:10 by volume of Skellysolve B/ethyl acetate using Merck silica gel): $R_f$ ca. 0.5.

Infrared (CHCl$_3$): ca. 1640 cm$^{-1}$ (vinyl), 1860, 1930 cm$^{-1}$ (alkane).

nmr (CDCl$_3$) (δ, ppm): 1.25 (s, methylene), 1.4–2.1 (m, cyclohexyl), 2.18, 2.3 (single peaks, complex, —CH$_2$CO—), 4.9–6.2 (m, vinyl).

EXAMPLE 6

3-Hydroxy-3-[10-(cyclohexyl)decyl]glutaric acid

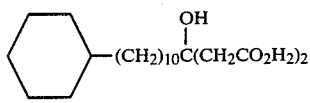

The bis-allyl carbinol (16.7 g), [See Example 5] is dissolved in a mixture of 200 ml each of dichloromethane and ethyl acetate and is cooled to ca. −60° to −30°. Ozone is bubbled into the solution until a blue color persists, ca. 2 hours. The solution is purged with oxygen (O$_2$) and then added dropwise, with stirring, to 60 ml of cold acetic acid. The solution is heated gently to distill off dichloromethane and then is allowed to cool. A solution of 20 ml of water, 40 ml of 10 percent sulfuric acid, 40 ml of 30 percent hydrogen peroxide, and 60 ml of acetic acid is added dropwise. The reaction mixture is heated to ca. 85° to boil off some of the solvent and then heated at reflux for ca. 2 hours. The solution is concentrated in vacuo and then diluted with 800 ml of water, producing an oily precipitate. The crude product is extracted into diethyl ether, which is washed three times with dilute sulfuric acid, then once with dilute sulfuric acid containing 20 percent sodium hydrogen sulfite, and again with dilute sulfuric acid, and then extracted twice into dilute sodium hydroxide. (The organic phase is dried, filtered, and concentrated to yield less than 1 g of an oil which is discarded). The sodium hydroxide extracts are combined and acidified, and the crude product is extracted into diethyl ether. After washing, the ether phase is dried and concentrated to 50 ml, cooled, diluted with Skellysolve A to 250 ml and allowed to crystallize. The sticky crystals, 15.2 g, are recrystallized from 100 ml of acetonitrile and yield 7.1 g of the desired product as a white powder. Structure assignment is supported by elemental analysis and by infrared and nmr spectroscopy.

tlc (50:48:2 by vol. of toluene/ethyl acetate/acetate acid using Merck silica gel): $R_f$ ca. 0.55.

Infrared (CHCl$_3$): ca. 1720 cm$^{-1}$ (carbonyl), ca. 2860, 3000 cm$^{-1}$ (alkane)

nmr (CDCl$_3$) (δ, ppm): 1.25 (s, methylene) over 0.9–1.9 (m, cyclohexyl), 2.70 (s, —CH$_2$CO$_2$—)

Elemental: Calcd. for C$_{21}$H$_{38}$O$_5$: C, 68.07; H, 10.35. Found: C, 66.75; 10.17.

EXAMPLE 7

3-Hydroxy-3-[10-phenylundecyl]glutaric acid

By substituting 20.4 g acetophenone for cyclohexanone in Example 2, and using 61.9 g the triphenylphosphonium bromide prepared in Example 1 from 10-bromo-decanoic acid, the sequence of Examples 2 and 3 will yield 22.1 g of methyl 10-phenylundec-9-enoate as a yellow oil, b.p. 133°–137°/0.07 mm whose structure assignment is supported by elemental analysis, and by infrared and nmr spectroscopy. Reduction of the double bond of 9.0 g of this material, using the conditions in Example 4, and carrying the intermediate through the steps of Examples 5 and 6 yields the desired product after crystallization from ether-Skellysolve B as a white powder, 1.85 g, having the formula:

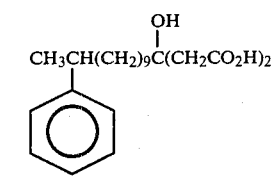

Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl), ca. 2860, 3000 cm$^{-1}$ (alkane).

nmr (CDCl$_3$) (δ, ppm): 1.25 (s, methylene) over 0.9–1.9 (m, cyclohexyl), 2.70 (s, —CH$_2$CO$_2$—), 7.2 (s, C$_6$H$_5$—).

Elemental: Calcd. for C$_{22}$H$_{34}$O$_5$: C, 69.81; H, 9.05. Found: C, 69.23; 9.22.

EXAMPLE 8

3-Hydroxy-3-[10-cyclohexylundecyl]glutaric acid

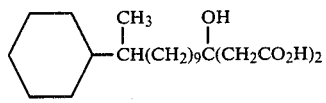

If 13.1 g of the methyl 10-phenylundec-9-enoate described in Example 7 is hydrogenated in tetrahydrofuran with 60 psi of hydrogen at 80° using 5% rhodium on carbon as catalyst until four molar-equivalents of hydrogen are taken up, both the chain-double bond and the phenyl ring will be reduced. The intermediate obtained, 11.9 g, is a water-white oil, b.p. 146°–152°/0.45 mm. Structure assignment is supported by elemental analysis and by infrared and nmr spectroscopy. When this material is reacted as in Examples 5 and 6, the desired product is obtained after crystallization from acetonitrile as a white powder, 7.7 g. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl), ca. 2860, 3000 cm$^{-1}$ (alkane).

nmr (CDCl$_3$) (δ, ppm): 1.25 (s, methylene) over 0.9–1.9 (m, cyclohexyl), 2.70 (s, —CH$_2$CO$_2$—).

Elemental: Calcd. for C$_{22}$H$_{40}$O$_5$: C, 68.71; H, 10.49. Found: C, 67.53, H, 10.24.

EXAMPLE 9

3-Hydroxy-3(9-(cyclohexyl)decyl)glutaric acid

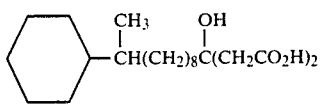

This acid is prepared by the method of Example 6 from the corresponding bis-allyl carbinol, which in turn is prepared by the methods of examples 5, 8, 3, and 2 from 10.0 g of acetophenone and 29.6 g of 9-(triphenylphosphonium)nonanoic acid bromide (prepared in Example 1). The product crystallizes from acetonitrile as a white powder, 3.86 g. Structure assignment is supported by elemental analysis and by infrared and nmr spectroscopy.

tlc (50:48:2 by vol. of toluene/ethyl acetate/acetic acid using Merck silica gel): $R_f$ ca. 0.65.

Infrared (CHCl$_3$): ca. 1720 cm$^{-1}$ (carbonyl), ca. 2860, 3000 cm$^{-1}$ (alkane).

nmr (CDCl$_3$ ($\delta$, ppm): 1.25 (s, methylene) over 0.9–1.9 (m, cyclohexyl), 2.70 (s, —CH$_2$CO$_2$—).

Elemental: Calcd. for C$_{21}$H$_{38}$O$_5$: C, 68.07; H, 10.35. Found: C, 67.87; 10.86.

EXAMPLE 10

3-Hydroxy-3-[11-(cyclohexyl)dodecyl]glutaric acid

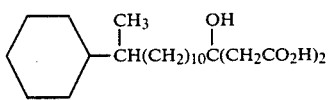

The dicarboxylic acid product is prepared by the method of Example 6 from the corresponding bis-allyl carbinol, which in turn is prepared by the methods of Examples 5, 8, 3 and 2 from 17.4 g of acetophenone and 54.5 g of 11-(triphenylphosphonium)undecanoic acid bromide. The product is isolated by crystallization from ether-Skellysolve as 8.9 g of a white powder. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl), ca. 2860, 3000 cm$^{-1}$ (alkane).

nmr (CDCl$_3$ ($\delta$, ppm): 1.25 (s, methylene) over 0.9–1.9 (m, cyclohexyl), 2.70 (s, —CH$_2$CO$_2$—).

Elemental: Calcd. for C$_{23}$H$_{42}$O$_5$: C, 69.30 H, 10.62. Found: C, 68.27; 10.45.

EXAMPLE 11

3-Hydroxy-3-[10-(1-methylcyclohexyl)decyl]glutaric acid, monomethyl ester

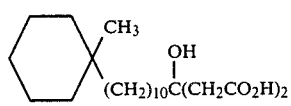

The dicarboxylic acid product is prepared by the method of Example 6 from the corresponding bis-allyl carbinol, which in turn is prepared by the methods of Examples 2, 3, 4, and 5 from 8.7 g of (1-methylcyclohexyl)carboxaldehyde and 24. g of 10-(triphenylphosphonium)decanoic acid bromide. The product crystallized from Skellysolve B as a white powder, 3.32 g. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl, ca. 2860, 3000 cm$^{-1}$ (alkane).

nmr (CDCl$_3$ ($\delta$, ppm): 1.25 (s, methylene) over 0.9–1.9 (m, cyclohexyl), 2.70 (s, —CH$_2$CO$_2$—).

Elemental: Calcd. for C$_{22}$H$_{40}$O$_5$: C, 68.71 H, 10.49. Found: C, 68.01; 10.33.

EXAMPLE 12

3-Hydroxy-3-(11-ethyltridecyl)glutaric acid

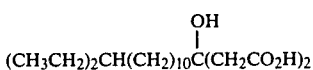

The dicarboxylic acid is prepared by the method of Example 6 from the corresponding bis-allyl carbinol, which in turn is prepared by the methods of Examples 2, 3, 4, and 5 from 12.5 g of 3-pentanone and 54.5 g of 11-(triphenylphosphonium)undecanoic acid bromide. The product is isolated by crystallization from Skellysolve A as 9.4 g of a white powder. Structure analysis is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$: ca. 1700 cm$^{-1}$ (carbonyl), ca. 2860, 2920, 3000 cm$^{-1}$ (alkane).

nmr (CDCl$_3$ ($\delta$, ppm): 0.80 (t, —CH$_3$), 1.25 (s, methylene), 1.0–1.8 (m, methylene), 2.54 (s, —CH$_2$CO$_2$—).

Elemental: Calcd. for C$_{20}$H$_{38}$O$_5$: C, 67.00; H, 10.68. Found: C, 66.70; H, 10.57.

EXAMPLE 13

3-Hydroxy-3-[8-(cyclohexyl)octyl]glutaric acid

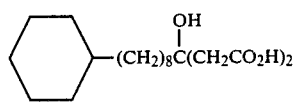

The dicarboxylic acid product is prepared by the method of Example 6 from the corresponding bis-allyl carbinol, which in turn is prepared by the methods of Examples 3, 8, and 5 from 9-phenylnonanoic acid. Crystallization of 30 percent diethyl ether in Skellysolve B is used to purify the product, isolated as 2.5 g of of white crystalline powder. Structure assignment is supported by elemental analysis and by infrared and nmr spectroscopy.

tlc (50:48:2 by vol. of toluene/ethyl acetate/acetic acid using Merck silica gel): $R_f$ ca. 0.4.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 1.25 (s, methylene) over 0.9–1.9 (m, cyclohexyl), 2.70 (s, —CH$_2$CO$_2$—).

Elemental: Calcd. for C$_{19}$H$_{34}$O$_5$: C, 66.63; H, 10.01 Found: C, 66.83; H, 9.82.

m.p.: 112°–116°.

EXAMPLE 14

3-Hydroxy-3-[9-(cyclohexyl)nonyl]glutaric acid

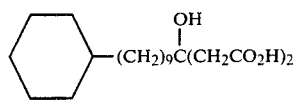

Starting with 30.8 g of 10-(triphenylphosphonium)-decanoic acid bromide and 8.2 g of cyclohexanone in Example 2, and carrying the intermediate through the methods of Examples 3, 4, 5 and 6, the desired glutaric acid is obtained as a white powder, 2.9 g, on crystallization from acetonitrile. Structure assignment is supported by elemental analysis and by infrared and nmr spectroscopy.

tlc (50:48:2 by vol. of toluene/ethyl acetate/acetic acid using Merck silica gel): $R_f$ ca. 0.5.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 1.25 (s, methylene) over 0.9–1.9 (m, cyclohexyl), 2.70 (s, —CH$_2$CO$_2$—).

Elemental: Calcd. for C$_{20}$H$_{36}$O$_5$: C, 67.37; H, 10.24. Found: C, 67.24; H, 10.27.

EXAMPLE 15

3-Hydroxy-3-[11-(cyclohexyl)undecyl]glutaric acid

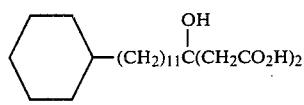

The dicarboxylic acid product is prepared by the method of Example 6 from the corresponding bis-allyl carbinol, which in turn is prepared by the methods of Examples 2, 3, 8, and 5 from 10.6 g benzaldehyde and 36.9 g of 11-(triphenylphosphonium)undecanoic acid bromide. The product is isolated by crystallization from ether-Skellysolve B as 3.3 g of a white powder. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 1.25 (s, methylene) over 0.9–1.9 (m, cyclohexyl), 2.70 (s, —CH$_2$CO$_2$—).

Elemental: Calcd. for C$_{22}$H$_{40}$O$_5$: C, 68.71; H, 10.49. Found: C, 67.82; H, 10.27.

EXAMPLE 16

3-Hydroxy-3-[13-(cyclohexyl)tridecyl]glutaric acid

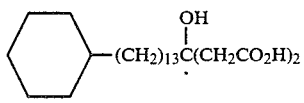

The dicarboxylic acid is prepared by the method of Example 6 from the corresponding bis-allyl carbinol, which in turn is prepared by the methods of Examples 2, 3, 8, and 5 from 19.2 g of cinnamaldehyde and 54.5 g of 11-(triphenylphosphonium)undecanoic acid bromide. (The cinnamyl double bond is also reduced during this process.) The product is isolated by crystallization from ether as 12.6 g of a white powder. Structure assignment is supported by elemental analysis and by infrared and nmr spectroscopy.

tlc (50:48:2 by vol. of toluene/ethyl acetate/acetic acid using Merck silica gel): $R_f$ ca. 0.7.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 1.25 (s, methylene) over 0.9–1.9 (m, cyclohexyl), 2.70 (s, —CH$_2$CO$_2$—).

Elemental: Calcd. for C$_{24}$H$_{44}$O$_5$: C, 69.86; H, 10.75. Found: C, 69.35; H, 11.02.

EXAMPLE 17

3-Hydroxy-3-[10,10-dimethylundecyl]glutaric acid

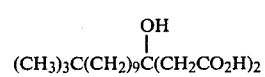

The dicarboxylic acid is prepared by the method of Example 6 from the corresponding bis-allyl carbinol, which in turn is prepared by the methods of Examples 2, 3, 4 and 5 from 3.0 g of pivalaldehyde and 11.6 g of 9-(triphenylphosphonium)nonanoic acid bromide. The product is isolated by crystallization from Skellysolve A as 0.55 g of a white powder. Structure analysis is supported by elemental assignment and by infrared and nmr spectroscopy.

tlc (50:48:2 by vol. of toluene/ethyl acetate/acetic acid using Merck silica gel): $R_f$ ca. 0.7.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 0.85 (s, t-butyl), 1.25 (s, methylene), 2.50 (s, —CH$_2$CO$_2$—).

Elemental: Calcd. for C$_{18}$H$_{34}$O$_5$: C, 65.42; H, 10.37. Found: C, 64.89; H, 10.51.

EXAMPLE 18

3-Hydroxy-3-[11,11-dimethyldodecyl]glutaric acid

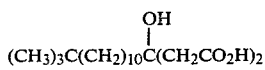

The dicarboxylic acid is prepared by the method of Example 6 from the corresponding bis-allyl carbinol, which in turn is prepared by the methods of Examples 2, 3, 4 and 5 from 5.7 g of pivalaldehyde and 24.4 g of 10-(triphenylphosphonium)decanoic acid bromide. The product is isolated by crystallization from ether-Skellysolve A as 7.4 g of a white powder. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca: 1720 cm$^{-1}$ (carbonyl), ca. 2860, 3000 cm$^{-1}$ (alkane).

nmr (CDCl$_3$ ($\delta$, ppm): 0.85 (s, t-butyl), 1.25 (s, methylene), 2.50 (s, —CH$_2$CO$_2$—).

Elemental: Calcd. for C$_{19}$H$_{36}$O$_5$: C, 66.24; H, 10.53. Found: C, 65.80; H, 10.77.

EXAMPLE 19

3-Hydroxy-3-[12,12-dimethyltridecyl]glutaric acid

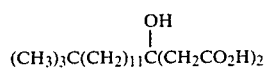

The dicarboxylic acid is prepared by the method of Example 6 from the corresponding bis-allyl carbinol, which in turn is prepared by the methods of Examples 2, 3, 4 and 5 from 12.5 g of pivalaldehyde and 54.5 g of 11-(triphenylphosphonium)undecanoic acid bromide. The product is isolated by crystallization from diethylether/Skellysolve A as 11.8 g of a white powder, m.p. 81°–3°. Structure assignment is supported by elemental analysis and by infrared and nmr spectroscopy.

tlc (50:48:2 by vol. of toluene/ethyl acetate/acetic acid using Merck silica gel): $R_f$ ca. 0.6.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 0.85 (s, t-butyl, 1.25 (s, methylene), 2.50 (s, —CH$_2$CO$_2$—).

Elemental: Calcd. for $C_{20}H_{38}O_5$: C, 67.00; H, 10.68. Found: C, 66.60; H, 10.66.

m.p. 81°–83°.

EXAMPLE 20

3-Hydroxy-3-[13,13-dimethyltetradecyl]glutaric acid

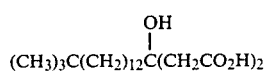

The dicarboxylic acid is prepared by the method of Example 6 from the corresponding bis-allyl carbinol, which in turn is prepared by the methods of Examples 2, 3, 4 and 5 from 5.0 g of pivalaldehyde and 22.6 g of 12-(triphenylphosphonium)dodecanoic acid bromide. The product is isolated by crystallization from 1:1 mixture (by volume) of Skellysolve-A and -B as 4.4 g of a white powder, m.p. 66°–71°. Structure assignment is supported by elemental analysis and by infrared and nmr spectroscopy.

tlc (50:48:2 by vol. of toluene/ethyl acetate/acetic acid using Merck silica gel): $R_f$ ca. 0.4.

Infrared (CHCl$_3$): ca. 1720 cm$^{-1}$ (carbonyl), ca. 2860, 3000 cm$^{-1}$ (alkane).

nmr (CDCl$_3$) ($\delta$, ppm): 0.85 (s, t-butyl), 1.25 (s, methylene), 2.50 (s, —CH$_2$CO$_2$—).

Elemental: Calcd. for $C_{21}H_{40}O_5 \cdot \frac{1}{2}H_2O$: C, 66.10; H, 10.83. Found: C, 66.21; H, 10.43.

m.p.: 66°–71°.

EXAMPLE 21

3-Hydroxy-3-[14,14-dimethylpentadecyl]glutaric acid

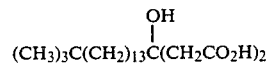

The dicarboxylic acid is prepared by the method of Example 6 from the corresponding bis-allyl carbinol, which in turn is prepared by the methods of Examples 2, 3, 4 and 5 from 4.7 g of t-butylacetaldehyde and 18.2 g of 12-(triphenylphosphonium)dodecanoic acid bromide. The product is isolated by crystallization from 1:1 mixture (by volume) of Skellysolve A as 1.37 g of a white powder. Structure assignment is supported by elemental analysis and by infrared and nmr spectroscopy.

tlc (50:48:2 by vol. of toluene/ethyl acetate/acetic acid using Merck silica gel): $R_f$ ca. 0.5.

Infrared (CHCl$_3$): ca. 1720 cm$^{-1}$ (carbonyl), ca. 2860, 3000 cm$^{-1}$ (alkane).

nmr (CDCl$_3$ ($\delta$, ppm): 0.85 (s, t-butyl), 1.25 (s, methylene), 2.50 (s, —CH$_2$CO$_2$—).

Elemental: Calcd. for $C_{22}H_{42}O_5$: C, 68.35; H, 10.95. Found: C, 68.27; H, 11.10.

CHART A

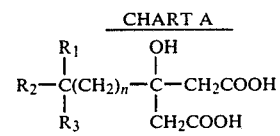

I

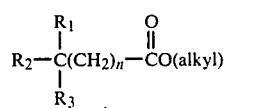

II

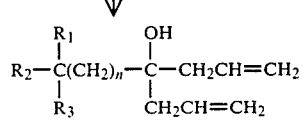

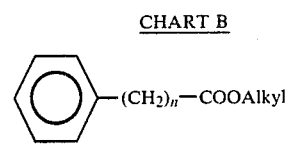

III $$\begin{array}{l} (1)\ O_3 \\ (2)\ H_2O_2 \end{array}$$

I

CHART B

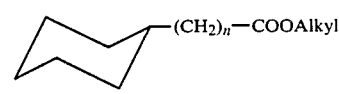

XI catalytic hydrogenation

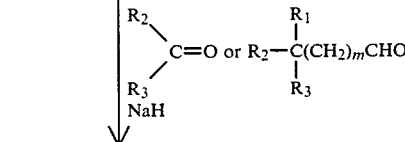

XII

Br—(CH$_2$)$_n$—CO$_2$H $\phi_3$P

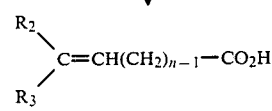

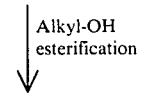

Alkyl-OH esterification

-continued
CHART B

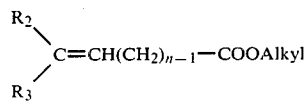

catalytic hydrogenation

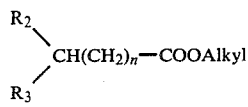

Where $R_1$, $R_2$, and $R_3$ are as have been defined previously and m is an integer of 0 or 1.

What we claim is:

1. A compound of the formula

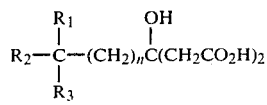

wherein
$R_1$, $R_2$, and $R_3$ are methyl and
n is an integer from 10 to 12 inclusive.

2. 3-Hydroxy-3-(11,11-dimethyldodecyl)glutaric acid, a compound according to claim 1.

3. 3-Hydroxy-3-(12,12-dimethyltridecyl)glutaric acid, a compound according to claim 1.

4. 3-Hydroxy-3-(13,13-dimethyltetradecyl)glutaric acid, a compound according to claim 1.

* * * * *

UNITED STATES PATENT AND TRADEMARK OFFICE
CERTIFICATE OF CORRECTION

PATENT NO. : 4,645,858
DATED : Feb. 24, 1987
INVENTOR(S) : Lowrie et al.

It is certified that error appears in the above-identified patent and that said Letters Patent are hereby corrected as shown below:

In the formula in Column 7, that portion of the formula reading "$(CH_2CO_2H_2)_2$" should read -- $(CH_2CO_2H)_2$ --.

Column 13, line 50, reading "$C_{21}H_{40}O_5.1/2H_2O$" should read -- $C_{21}H_{40}O_5 \cdot 1/2H_2O$ --.

Signed and Sealed this

Sixteenth Day of February, 1988

Attest:

DONALD J. QUIGG

Attesting Officer        Commissioner of Patents and Trademarks